United States Patent
Eil et al.

(10) Patent No.: US 10,888,458 B2
(45) Date of Patent: Jan. 12, 2021

(54) COMBINED NEAR INFRARED IMAGING AND VISIBLE IMAGING IN A COMPACT MICROSCOPE STACK

(71) Applicant: NOVARTIS AG, Basel (CH)

(72) Inventors: Martin Eil, Berlin (DE); Mauricio Jochinsen, Fountain Valley, CA (US); Hugang Ren, Pleasanton, CA (US); Lingfeng Yu, Rancho Santa Margarita, CA (US)

(73) Assignee: Alcon Inc.

( * ) Notice: Subject to any disclaimer, the term of this patent is extended or adjusted under 35 U.S.C. 154(b) by 21 days.

(21) Appl. No.: 16/209,502

(22) Filed: Dec. 4, 2018

(65) Prior Publication Data

US 2019/0175402 A1  Jun. 13, 2019

Related U.S. Application Data

(60) Provisional application No. 62/597,630, filed on Dec. 12, 2017.

(51) Int. Cl.
*A61F 9/008* (2006.01)
*A61B 3/12* (2006.01)
(Continued)

(52) U.S. Cl.
CPC .......... *A61F 9/00736* (2013.01); *A61B 3/102* (2013.01); *A61B 3/12* (2013.01); *A61B 3/13* (2013.01); *A61B 90/20* (2016.02); *A61F 9/00812* (2013.01); *G02B 21/0012* (2013.01); *G02B 21/20* (2013.01); *A61B 2090/371* (2016.02); *A61B 2090/3735* (2016.02); *A61F 2009/0087* (2013.01); *A61F 2009/00851* (2013.01); *A61F 2009/00887* (2013.01); *A61F 2009/00897* (2013.01)

(58) Field of Classification Search
CPC ...... A61B 2090/371; A61B 2090/3735; A61B 3/102; A61B 3/12; A61B 3/13; A61B 90/20; A61F 2009/00851; A61F 2009/0087; A61F 2009/00887; A61F 2009/00897; A61F 9/00736; A61F 9/00812; G02B 21/0012; G02B 21/20; G02B 21/22; G02B 21/361
See application file for complete search history.

(56) References Cited

U.S. PATENT DOCUMENTS

| | | |
|---|---|---|
| 2010/0182418 A1 | 7/2010 | Jess et al. |
| 2012/0002030 A1 | 1/2012 | Kalkbrenner et al. |

(Continued)

FOREIGN PATENT DOCUMENTS

WO  2017/189283 A1  11/2017

*Primary Examiner* — George Manuel
(74) *Attorney, Agent, or Firm* — Joseph Weatherbee, Esq.

(57) ABSTRACT

Both visible and IR cameras are integrated without an increase in an optical stack height of a surgical microscope used for ophthalmic surgery. The IR camera may be used to directly and intraoperatively capture a scanning OCT measurement beam, which uses NIR light that is invisible to the human eye. An IR image from the IR camera taken from the same surgical field as displayed intraoperatively to a user of the surgical microscope may be displayed in an ocular to the user, enabling visualization of a location of an OCT scan along with actual visible images of the surgical field.

20 Claims, 11 Drawing Sheets

(51) Int. Cl.
*A61F 9/007* (2006.01)
*G02B 21/20* (2006.01)
*G02B 21/00* (2006.01)
*A61B 3/10* (2006.01)
*A61B 90/20* (2016.01)
*A61B 3/13* (2006.01)
*A61B 90/00* (2016.01)

(56) References Cited

U.S. PATENT DOCUMENTS

| | | |
|---|---|---|
| 2012/0184846 A1 | 7/2012 | Izatt |
| 2014/0188093 A1 | 7/2014 | Kurtz et al. |
| 2015/0077705 A1 | 3/2015 | Artsyukhovich et al. |
| 2015/0272438 A1* | 10/2015 | Yao .......................... A61B 3/12 |
| | | 351/206 |
| 2017/0049322 A1 | 2/2017 | Heeren et al. |
| 2017/0156588 A1 | 6/2017 | Ren et al. |

* cited by examiner

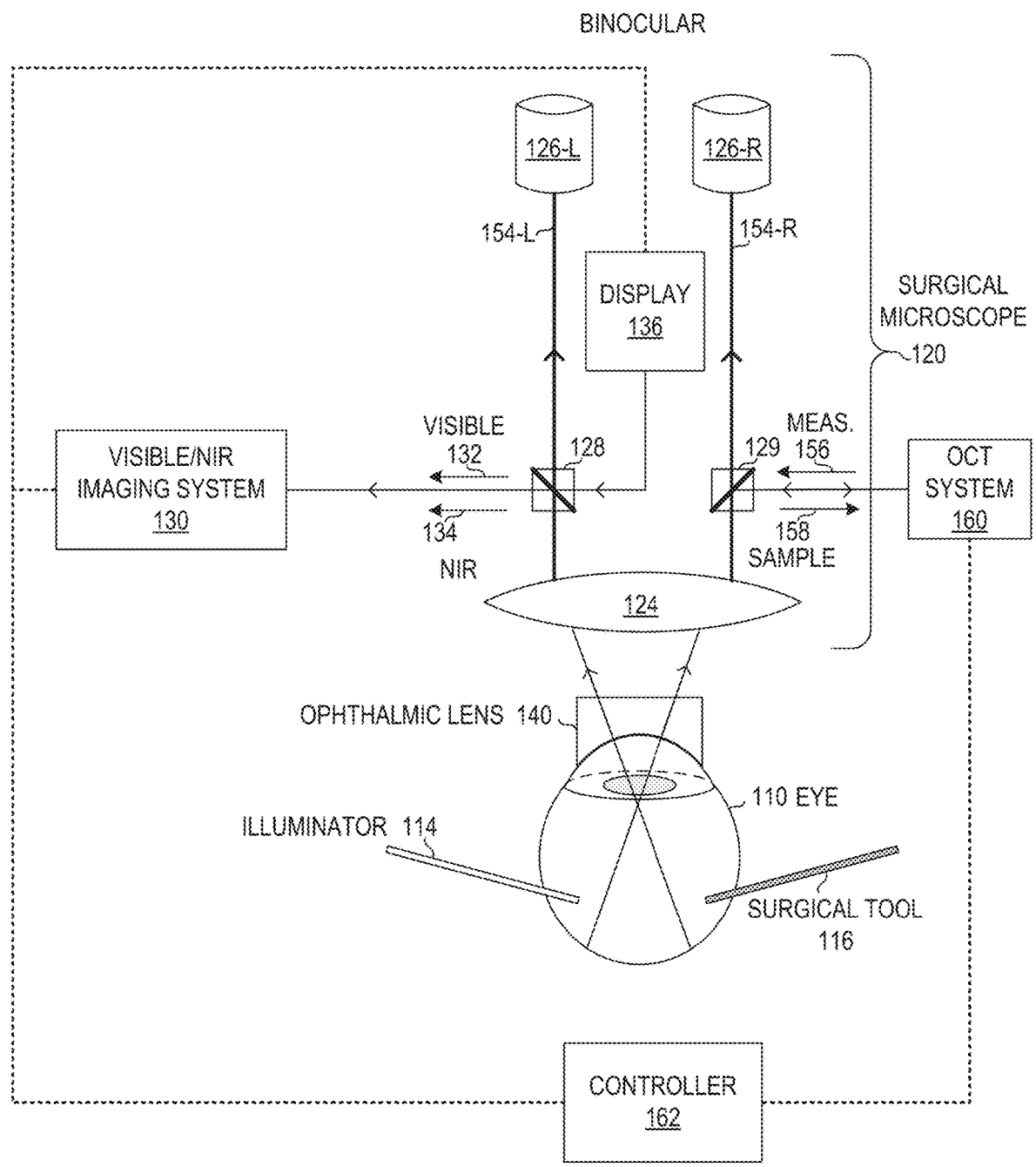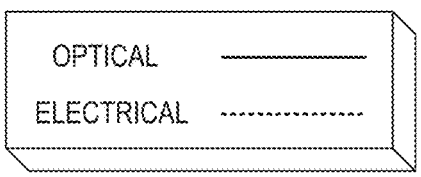
FIG. 1

500 — METHOD FOR PERFORMING OPHTHALMIC SURGERY

502 SCANNING A SURGICAL FIELD USING AN OCT SCANNING SYSTEM COUPLED TO A SURGICAL MICROSCOPE, THE SURGICAL MICROSCOPE USED TO VIEW VISIBLE LIGHT FROM THE SURGICAL FIELD, WHERE THE OCT SCANNING SYSTEM PROJECTS NIR LIGHT ONTO THE SURGICAL FIELD FOR THE SCANNING OF THE SURGICAL FIELD

504 DIVERTING, USING A MULTI-BEAM SPLITTER IN AN OPTICAL PATH TRANSMITTING THE VISIBLE LIGHT TO A FIRST OCULAR OF THE SURGICAL MICROSCOPE, A FIRST PORTION OF THE NIR LIGHT AND A SECOND PORTION OF THE VISIBLE LIGHT TO AN IMAGING PATH OF THE SURGICAL MICROSCOPE, WHERE THE IMAGING PATH IS IN A PLANE PERPENDICULAR TO THE OPTICAL PATH

506 SPLITTING, USING A DICHROIC MIRROR IN THE IMAGING PATH, THE FIRST PORTION OF THE NIR LIGHT FROM THE SECOND PORTION OF THE VISIBLE LIGHT

508 GENERATING AN IR IMAGE OF THE SURGICAL FIELD FROM THE FIRST PORTION OF THE NIR LIGHT USING AN IR CAMERA, THE IR IMAGE INDICATING A LOCATION IN THE SURGICAL FIELD OF THE SCANNING OF THE SURGICAL FIELD

510 GENERATING A VISIBLE IMAGE OF THE SURGICAL FIELD FROM THE SECOND PORTION OF THE VISIBLE LIGHT USING A VISIBLE CAMERA, WHERE THE VISIBLE CAMERA AND THE IR CAMERA ARE POSITIONED IN THE PLANE

512 SENDING THE ACQUIRED IR IMAGE TO A DISPLAY USED TO OUTPUT DISPLAY LIGHT FOR VIEWING AT A SECOND OCULAR OF THE SURGICAL MICROSCOPE, WHERE AT LEAST A PORTION OF THE DISPLAY LIGHT FOLLOWS A PATH OF VISIBLE LIGHT TRANSMITTED TO THE SECOND OCULAR

514 SENDING THE ACQUIRED VISIBLE IMAGE TO THE DISPLAY, WHERE AT LEAST A PORTION OF THE DISPLAY LIGHT FOLLOWS THE PATH OF THE VISIBLE LIGHT TRANSMITTED TO THE SECOND OCULAR

FIG. 5

COMBINED NEAR INFRARED IMAGING AND VISIBLE IMAGING IN A COMPACT MICROSCOPE STACK

BACKGROUND

Field of the Disclosure

The present disclosure relates to ophthalmic surgery, and more specifically, to combined near infrared imaging and visible imaging in a compact microscope stack.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures, and may encompass vitreoretinal surgery and cataract surgery, among others. Specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others. During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during ophthalmic surgery. The patient typically lies supine under the surgical microscope during surgery and a speculum is used to keep the eye exposed. Depending on a type of optical system used, the ophthalmologist has a given field of view of the fundus, which may vary from a narrow field of view to a wide field of view that can extend to peripheral regions of the fundus.

During cataract surgery, which is performed on the anterior portion of the eye that is externally visible, a diseased lens may be removed from the lenticular bag and replaced with an artificial lens, such as an intraocular lens (IOL). During cataract surgery, the cornea and the iris may be viewed using a surgical microscope to enable implantation of the artificial lens through an incision in the cornea, as well as to align and properly seat the new artificial lens.

In addition to viewing the eye using visible light, surgical microscopes may be equipped with optical coherence tomography (OCT) systems to provide additional information about non-visible portions of eye tissue involved with the ophthalmic surgery. The OCT system may also enable imaging of portions of the eye that are otherwise difficult to optically distinguish under visible light using the surgical microscope. An OCT image provided by the OCT system may guide the surgeon during the ophthalmic surgical procedure, but because OCT typically operates with non-visible light, such as near-infrared (NIR) light, correlating a position of an OCT measurement beam to actual locations in the eye being viewed using the surgical microscope may be difficult.

SUMMARY

In one aspect, a disclosed method is for performing ophthalmic surgery using a surgical microscope. The method may include scanning a surgical field using an OCT scanning system coupled to a surgical microscope, the surgical microscope used to view visible light from the surgical field. In the method, the OCT scanning system may project NIR light onto the surgical field for the scanning of the surgical field. The method may further include diverting, using a multi-beam splitter in an optical path transmitting the visible light to a first ocular of the surgical microscope, a first portion of the NIR light and a second portion of the visible light to an imaging path of the surgical microscope. In the method, the imaging path may be in a plane perpendicular to the optical path. The method may also include splitting, using a dichroic mirror in the imaging path, the first portion of the NIR light from the second portion of the visible light, and generating an IR image of the surgical field from the first portion of the NIR light using an IR camera, the IR image indicating a location in the surgical field of the scanning of the surgical field. The method may also include generating a visible image of the surgical field from the second portion of the visible light using a visible camera, where the visible camera and the IR camera are positioned in the plane.

In any of the disclosed implementations, the method may include acquiring the IR image from the IR camera, and sending the IR image to a controller to generate display light for viewing at a second ocular of the surgical microscope. In the method, at least a portion of the display light may follow a path of visible light transmitted to the second ocular.

In any of the disclosed implementations, the method may include acquiring the visible image from the visible camera, and sending the visible image to the controller to generate the display light In the method, at least a portion of the display light may follow the path of the visible light transmitted to the second ocular.

In any of the disclosed implementations of the method, the first ocular and the second ocular may be the same ocular and the display light may be reflected by the multi-beam splitter onto the optical path.

In any of the disclosed implementations of the method, the first ocular and the second ocular may be different oculars and the display light may be reflected by a beam combiner onto the visible light transmitted to the second ocular.

In any of the disclosed implementations, the method may include splitting the display light into a first display beam and a second display beam using a first beam splitter, directing the first display beam to the first ocular using the multi-beam splitter, and directing the second display beam to the second ocular using the beam combiner.

In any of the disclosed implementations of the method, the first portion may be at least 90% of the NIR light, while the second portion may be less than or equal to 30% of the visible light.

In any of the disclosed implementations of the method, the visible camera and IR camera may be oriented perpendicular to each other.

In any of the disclosed implementations, the method may include diverting, using a second multi-beam splitter in a second optical path transmitting visible light to a second ocular of the surgical microscope different from the first ocular, a third portion of the NIR light and a fourth portion of the visible light to a second imaging path of the surgical microscope, where the imaging path and the second imaging path are in the plane. The method may further include splitting, using a second dichroic mirror in the second imaging path, the third portion of the NIR light from the fourth portion of the visible light, generating a second IR image of the surgical field from the third portion of the NIR light using a second IR camera, the second IR image indicating the location in the surgical field of the scanning of the surgical field, and generating a second visible image of the surgical field from the fourth portion of the visible light using a second visible camera, where the second visible camera and the second IR camera are positioned in the plane.

In any of the disclosed implementations, the method may include acquiring the second IR image from the second IR camera, sending the second IR image to the controller to generate second display light for viewing at the second ocular. In the method, at least a portion of the second display light including the second IR image may follow a path of the visible light transmitted to the second ocular. The method may further include acquiring the second visible image from the second visible camera, and sending the second visible image to the controller to generate the second display light. In the method, at least a portion of display light including the second visible image may follow the path of the visible light transmitted to the second ocular.

In a further aspect, a surgical microscope for performing ophthalmic surgery is disclosed. The surgical microscope may include an OCT scanning system coupled to the surgical microscope and used for scanning a surgical field, the surgical microscope used to view visible light from the surgical field. In the surgical microscope, the OCT scanning system may project NIR light onto the surgical field for the scanning of the surgical field. The surgical microscope may further include a multi-beam splitter in an optical path transmitting the visible light to a first ocular of the surgical microscope, the multi-beam splitter used to divert a first portion of the NIR light and a second portion of the visible light to an imaging path of the surgical microscope, where the imaging path is in a plane perpendicular to the optical path. The surgical microscope may further include a dichroic mirror in the imaging path used for splitting the first portion of the NIR light from the second portion of the visible light, an IR camera used to generate an IR image of the surgical field from the first portion of the NIR light, the IR image indicating a location in the surgical field of the scanning of the surgical field, and a visible camera used to generate a visible image of the surgical field from the second portion of the visible light, where the visible camera and the IR camera are positioned in the plane.

In any of the disclosed implementations, the surgical microscope may include a controller used to acquire the IR image from the IR camera and generate overlay information, and a display receiving the overlay information from the controller, the display used to output display light for viewing at a second ocular of the surgical microscope. In the surgical microscope, at least a portion of the display light may follow a path of visible light transmitted to the second ocular.

In any of the disclosed implementations, the surgical microscope may include the controller used to acquire the visible image from the visible camera, and the display receiving the visible image from the controller. In the surgical microscope, at least a portion of the display light including the visible image may follow the path of visible light transmitted to the second ocular.

In any of the disclosed implementations of the surgical microscope, the first ocular and the second ocular may be the same ocular and the display light may be reflected by the multi-beam splitter onto the optical path.

In any of the disclosed implementations of the surgical microscope, the first ocular and the second ocular may be different oculars, while the surgical microscope may further include a beam combiner used to reflect the display light onto the visible light transmitted to the second ocular.

In any of the disclosed implementations, the surgical microscope may include a first beam splitter used to split the display light into a first display beam and a second display beam, the multi-beam splitter used to direct the first display beam to the first ocular, and the beam combiner used to direct the second display beam to the second ocular.

In any of the disclosed implementations of the surgical microscope, the first portion may be at least 90% of the NIR light, while the second portion may be less than or equal to 30% of the visible light.

In any of the disclosed implementations of the surgical microscope, the visible camera and IR camera may be oriented perpendicular to each other.

In any of the disclosed implementations, the surgical microscope may include a second multi-beam splitter in a second optical path transmitting visible light to a second ocular of the surgical microscope different from the first ocular, the second multi-beam splitter used to divert a third portion of the NIR light and a fourth portion of the visible light to a second imaging path of the surgical microscope, where the imaging path and the second imaging path are in the plane. The surgical microscope may further include a second dichroic mirror in the second imaging path, the second dichroic mirror used to divert the third portion of the NIR light from the fourth portion of the visible light, a second IR camera used to generate a second IR image of the surgical field from the third portion of the NIR light, the second IR image indicating the location in the surgical field of the scanning of the surgical field, and a second visible camera used to generate a second visible image of the surgical field from the fourth portion of the visible light, where the second visible camera and the second IR camera are positioned in the plane.

In any of the disclosed implementations, the surgical microscope may include the controller used to acquire the second IR image from the second IR camera and generate the overlay information, a second display receiving overlay information from the controller, the second display used to output second display light for viewing at the second ocular. In the surgical microscope, at least a portion of the second display light may follow a path of the visible light transmitted to the second ocular. The surgical microscope may further include the controller used to acquire the second visible image from the second visible camera and generate the overlay information, and the second display receiving the overlay information from the controller. In the surgical microscope, at least a portion of the second display light may follow the path of the visible light transmitted to the second ocular.

BRIEF DESCRIPTION OF THE DRAWINGS

For a more complete understanding of the present disclosure, reference is now made to the following description, taken in conjunction with the accompanying drawings, in which:

FIG. 1 is a depiction of selected elements of a surgical microscopy scanning instrument;

FIG. 5 is a flow chart of a method for performing ophthalmic surgery;

Figure 2A:
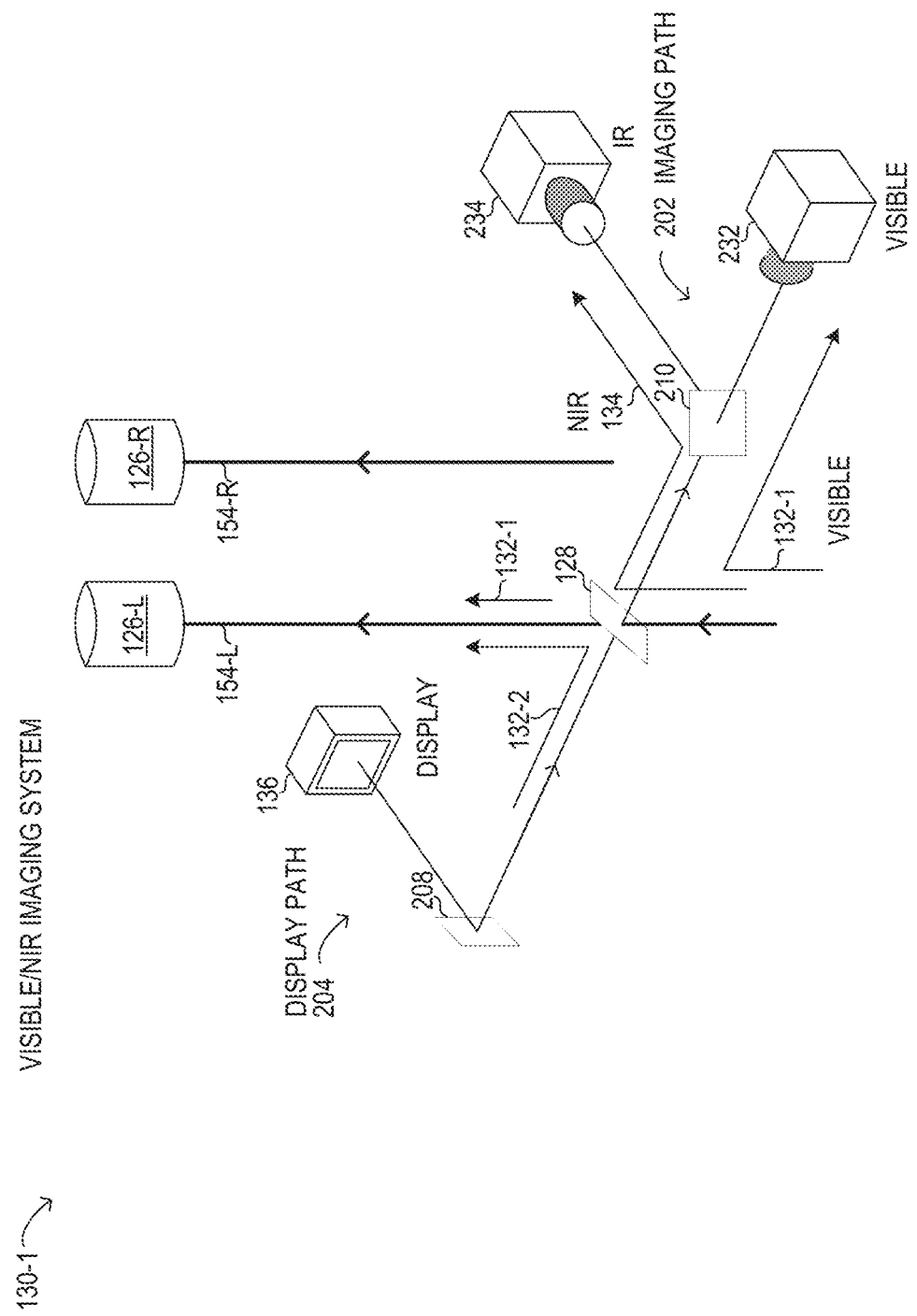
FIGS. 2A, 2B, 2C, and 2D are depictions of selected elements of different visible/NIR imaging systems.

DESCRIPTION OF PARTICULAR
IMPLEMENTATIONS

In the following description, details are set forth by way of example to facilitate discussion of the disclosed subject matter. It should be apparent to a person of ordinary skill in the field, however, that the disclosed implementations are exemplary and not exhaustive of all possible implementations.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during ophthalmic surgery, such as vitreoretinal surgery or cataract surgery, a surgeon may view a portion of an eye of a patient using a surgical microscope. For example, during vitreoretinal surgery the fundus may be viewed in conjunction with an ophthalmic lens for viewing through the cornea, such as a contact or non-contact lens. During cataract surgery, the anterior portion of the eye may be viewed through the cornea using a surgical microscope. In order to perform any of a variety of surgical procedures, the surgeon may desire to optically scan certain portions of the eye to generate profile depth scans of the corresponding eye tissue, such as by using an OCT system to scan the eye tissue and generate an OCT image therefrom. The profile depth scans may reveal information about eye tissue that is not readily visible from optical images generated by the surgical microscope. The profile depth scans may be point scans (A-scan), line scans (B-scan), or area scans (C-scan). An image from a B-scan will image the depth of eye tissue along a line, while a C-scan results in 3-dimensional (3D) data that can be sectioned to provide various views, including an en face view from the optical view perspective, but which can be generated at various depths and for selected tissue layers.

Although OCT systems have been integrated with the optics of surgical microscopes, OCT systems (comprising scanners and scanning controllers) typically are not inherently correlated with the visible images of the surgical field provided by the surgical microscope. Thus, additional methods and systems are used to correlate a position of a non-visible OCT measurement beam within a surgical field being viewed using visible light. Location indicators, such as an aiming laser beam of visible light, are known that indicate an intraoperative position of an OCT measurement beam on a visible image of a surgical field. However, such location indicators may not be widely useful across different microscope designs having different optical zoom or magnification levels, and may be inflexibly constrained in application, which is undesirable.

As will be described in further detail, a combined near infrared imaging and visible imaging in a compact microscope stack is disclosed that provides an infrared (IR) camera to directly capture an IR image of a NIR OCT measurement beam in the surgical field viewed by a surgical microscope. The IR camera is provided in addition to a visible camera to enable digital visualization of image content, visible imaging, and NIR imaging without increasing the stack height between oculars and objective lenses of the surgical microscope, because an increased stack height can reduce the ergonomic usability of the surgical microscope. In the combined near infrared imaging and visible imaging in a compact microscope stack disclosed herein, the direct capture of the OCT measurement beam using the IR camera enables flexible and unconstrained operation with a variety of microscope designs, objectives, and magnification levels. In the combined near infrared imaging and visible imaging in a compact microscope stack disclosed herein, the IR camera and the visible camera are integrated using an imaging path of light that is perpendicular to the stack height, and so, does not increase the stack height. The combined near infrared imaging and visible imaging in a compact microscope stack disclosed herein allows the surgeon to quickly and accurately determine locations of the OCT measurement beam within the surgical field in order to correlate the locations of the OCT measurement beam to locations of eye tissue subject to a surgical intervention. By avoiding unwieldy and time-consuming operations involved with manually correlating the location of the OCT measurement beam to locations of eye tissue, the combined near infrared imaging and visible imaging in a compact microscope stack disclosed herein may improve surgical workflow and positively impact patient safety.

Referring now to the drawings, FIG. 1 is depiction of a surgical microscopy scanning instrument 100. Instrument 100 is not drawn to scale or perspective but is a schematic representation. As will be described in further detail, instrument 100 may be used during ophthalmic surgery, such as vitreoretinal surgery, to view and analyze a human eye 110 of a patient. As shown, instrument 100 includes a surgical microscope 120, an OCT system 160, and a controller 162. Also shown in FIG. 1 are a visible/NIR imaging system 130, a display 136, an ophthalmic lens 140, as well as surgical tool 116 and illuminator 114. It is noted that microscopy scanning instrument 100 may be implemented with different elements in various implementations.

As shown in FIG. 1, surgical microscope 120 is depicted in schematic form to illustrate optical and electrical functionality, as indicated. It will be understood that surgical microscope 120 may include various other electronic and mechanical components, in different implementations. Accordingly, an objective 124 may represent a selectable objective to provide a desired magnification or field of view of the fundus of eye 110. Objective 124 may receive light from the fundus of eye 110 via ophthalmic lens 140 that rests on the cornea of eye 110. Although ophthalmic lens 140 is shown as a contact lens for descriptive purposes, it is noted that various types of ophthalmic lenses may be used with surgical microscope 120, including contact lenses and non-contact lenses. To perform vitreoretinal surgery, various tools and instruments may be used, including tools that penetrate the sclera, represented by surgical tool 116. Illuminator 114 may be a special tool that provides a light source from within the fundus of eye 110, among other light sources that may be used.

In FIG. 1, surgical microscope 120 is shown with a binocular arrangement with two distinct but substantially equal light paths 154 that enable viewing with binoculars 126 that comprise a left ocular 126-L and a right ocular 126-R. A user (not shown) of instrument 100, such as a surgeon or other medical professional, can visualize a surgical field corresponding to a field of view of surgical microscope 120. During the ophthalmic surgery, surgical tool 116 may be inserted into eye 110. In a vitrectomy procedure, for example, surgical tool 116 may be inserted into the vitreous chamber via an incision through the sclera in the pars plana. Surgical tool 116 may be a cutting probe, a vitrectomy probe, a laser probe, an ablation probe, a vacuum probe, a flushing probe, scissors, forceps, other suitable ophthalmic devices, or various combinations thereof. Various other surgical tools, such as illuminator 114 or an infusion cannula, among others, may also be inserted into eye 110 during ophthalmic surgery. The user may perform the ophthalmic surgery in the surgical field using surgical tool 116. The surgical field may include various biological tissue in eye 110, including the vitreous humor, transparent membranes, blood vessels, retina, macula, foveola, fovea centralis, para fovea, perifovea, optic disc, optic cup, or other portions of eye 110. The biological tissue may also include various layers of the retina, including the inner limiting membrane, nerve fiber layer, ganglion cell layer, inner plexiform layer, inner nuclear layer, outer plexiform layer, outer nuclear layer, external limiting membrane, layer of rods and cones, or retinal pigment epithelium.

As noted above, surgical microscope 120 is used to image the surgical field during ophthalmic surgery. Surgical microscope 120 may be any suitable surgical microscope configured for use during an ophthalmic surgery. The surgical microscope may include analog or digital optical components or combinations thereof. Accordingly, surgical microscope 120 may include various internal lenses (not shown), such as a focusing lens, a zoom lens, along with objective lens 124. Surgical microscope 120 may further comprise various different mirrors, filters, gratings, or other optical components that comprise an optical train. In operation with visible light, surgical microscope 120 may receive visible light reflected from the surgical field and be used to view a visible image corresponding to the visible light using at least one ocular 126 that provides for viewing by an eye of the user. The visible image may comprise an en face, fundus image of the surgical field. In the stereoscopic configuration shown in FIG. 1, surgical microscope 120 is depicted with two optical paths 154 from objective 124 to ocular 126. Specifically, a left optical path 154-L transmits light to a left ocular 126-L, while a right optical path 154-R transmits light to a right ocular 126-R. As described herein, optical paths 156 may be used to transmit direct images from objective 124 of the surgical field and digital images of the surgical field generated by display 136. The digital images of the surgical field may further comprise visible images and IR images of the surgical field, which are respectively generated by a visible light camera and an IR camera included in visible/NIR imaging system 130, as explained in further detail herein. It is noted that the designations of left and right, as used herein, may be arbitrary and may be interchangeable and may be specified herein for descriptive purposes of reference to FIG. 1.

In FIG. 1, OCT system 160 may include various components, including an OCT beam source, a collimator, a scanner, and optics including lenses, mirrors, filters, and gratings associated with a reference arm and a sample arm. The OCT beam source may output OCT measurement beam 156 that is directed by the scanner to scan anatomy within the surgical field of surgical microscope 120. The scanner may include one or more of a scanning mirror, a micromirror device, a micro-electro-mechanical system (MEMS) device, a deformable platform, a galvanometer-based scanner, a polygon scanner, or a resonant piezoelectric lead zirconate titanate (PZT) scanner. The scanner may be used to direct OCT measurement beam 156 in any suitable scan pattern of eye tissue. OCT measurement beam 156 may include light a wavelength in the NIR range, such as in a 0.2-1.8 micron range, a 0.7-1.4 micron range, or a 0.9-1.1 micron range. When OCT measurement beam 156 employs NIR light, the location at which OCT measurement beam 156 scans the eye tissue will not be visible to the naked eye, which is disadvantageous for the user of surgical microscope 120.

OCT system 160 further includes a detector configured to detect an interference pattern based on path length differences in OCT sample beam 158. The detector may include a balanced photo-detector, an InGaAs PIN detector, an InGaAs detector array, a Si PIN detector, charge-coupled devices (CCD) sensor, complementary metal-oxide-semiconductor (CMOS) sensor, pixels, or an array of any other type of sensor that generates an electric signal based on detected light. Further, the detector may include a two-dimensional sensor array or a detector camera.

In FIG. 1, OCT system 160 may be a Fourier domain system (spectral domain, swept-source, among others) or a time domain system. In a time domain OCT system, a reference arm is moved to different distances from the OCT beam source, allowing imaging of the target biological tissue at different depths. In a frequency domain OCT system, spatially-encoded frequency domain (SEFD) system, spectral domain system, or Fourier domain system, the depth scan of the target biological tissue can be obtained by analyzing an interference signal based on the wavelength of light. Because the frequency domain OCT system does not involve movement of physical components (compared to the reference arm in a time domain OCT system), the scanning speed of the frequency domain OCT system may be faster than in a time domain system. The SEFD system can utilize a dispersive detector to break up an OCT beam into beams of different wavelengths. The OCT beam source in a swept-source (SS-OCT) system can utilize a tunable laser that rapidly sweeps across different wavelengths, and can be used to obtain up to 100,000 A-scans per second.

OCT system 160 may be optically integrated by using various methods into surgical microscope 120. As shown in FIG. 1, a partial mirror 129 may be used to divert incoming OCT measurement beam 156 from OCT system 160 to right optical path 154-R, where OCT measurement beam 156 is directed by objective lens 124 and ophthalmic lens 140 to an interior portion of eye 110. Partial mirror 129 may be dichroic and may selectively reflect NIR light, while selectively transmitting visible light. Thus, visible light emerging from eye 110 and being carried along right optical path 154-R may be transmitted by partial mirror 129 towards right ocular 126-R, while NIR light reflected from OCT measurement beam 156 may be reflected back to OCT system 160 as an OCT sample beam 158 that includes photons from OCT measurement beam 156. Because OCT system 160 (and in particular the OCT scanner included with OCT system 160) is mounted in a fixed arrangement, when OCT measurement beam 156 is scanned, different locations in the surgical field are scanned and reflect OCT sample beam 158 back to OCT system 160 for detection and imaging.

Thus, OCT system 160 is used to receive OCT sample beam 158 reflected from the target biological tissue in the surgical field and to generate an OCT image. OCT system 160 may generate the OCT image based on scanning the surgical field. Specifically, the OCT image may be comprised of individual A-scans that image a certain depth of tissue at a single point in the surgical field. Multiple, adjacent A-scans can be combined to form a B-scan as a line scan of the plurality of A-scans. The B-scan may generate a two-dimensional OCT image of the line scan and the depth of the tissue. A C-scan may generate a three-dimensional OCT image from a plurality of adjacent B-scans.

As explained above, OCT system 160 may be integrated with surgical microscope 120 be used to scan the surgical field to generate OCT images. In particular, OCT system 182 may provide non-contact high resolution and depth-resolved imaging capability during ophthalmic surgery. Controller 162 may be further used to overlay or 'inject' at least a portion of the OCT image into a visible image viewed at ocular 154. For example, controller 162 may receive the OCT image from OCT system 160 and may cause the OCT image to be output by display 136. Then, an image representing overlay information (such as the location of the OCT NIR light) may be output to a multi-beam splitter 128 having various functionality as explained in further detail below, where the image is reflected onto left optical path 154-L and transmitted to left ocular 154-L for viewing by the user. This image may be a cross-sectional OCT image that is overlaid onto the field of view of surgical microscope 120 (the surgical field), which allows the user (a surgeon) to view the cross-sectional OCT image as well as the visible image of the surgical field from objective lens 124 as an enface, fundus image. The cross-sectional OCT image may show anatomical features within tissue of the eye that may not be visible in the enface, fundus image.

In addition to the overlay of cross-sectional OCT images described above, visible/NIR imaging system 130 may be used to digitally generate a visible image and an IR image of the surgical field. In particular the IR image may be used to show an actual location of OCT measurement beam 156 scanning a desired interior portion of eye 110 within the surgical field. Specifically, reflected NIR light 134 from OCT measurement beam 156 may arrive at multi-beam splitter 128, in a substantially similar manner as OCT sample beam 158 arrives at partial mirror 129. However, instead of using NIR light 134 for OCT imaging of a depth of tissue (as with OCT sample beam 158), NIR light 134 may be acquired by an IR camera included in visible/NIR imaging system 130 and used to create an IR image that shows the actual location of OCT measurement beam 156 in the surgical field. Because the IR image is generated using a separate IR camera and with the optics of surgical microscope 120, the arrangement shown in FIG. 1 may be used with different types of surgical microscopes and with any magnification level.

Specifically in FIG. 1, from objective 124 visible light 132 and NIR light 134 may arrive at multi-beam splitter 128 from the interior portion of eye 110. Multi-beam splitter 128 may be constructed to selectively reflect a large portion of NIR light 134 arriving along left optical path 154-L from objective lens 124, thereby diverting NIR light 134 to visible/NIR imaging system 130. At the same time, multi-beam splitter 128 may be constructed to selectively reflect a small portion of visible light 132 arriving along left optical path 154-L from objective lens 124, while transmitting a large portion of visible light 132 towards left ocular 126-L. In some implementations, NIR light 134 reflected from multi-beam splitter 128 may be greater than 90% of the incident NIR light, while visible light 134 reflected from multi-beam splitter 128 may be about 30% of the incident visible light. As noted above, multi-beam splitter 128 may additionally be reflective to visible light from display 136 arriving at an opposite face to reflect the visible light from display 136 towards left ocular 126-L along left optical path 125-L. It is noted that various filters may be used in order to balance visible light levels observed between left ocular 126-L and right ocular 126-R to provide a balanced stereoscopic view when different intensities of visible light are transmitted by left optical path 154-L and right optical path 154-R. It is noted that the optical arrangement depicted in FIG. 1 is exemplary and may be different in other implementations.

Then, visible/NIR imaging system 130 may receive NIR light 134 and visible light 132 from multi-beam splitter 128. Visible/NIR imaging system 130 and may internally direct NIR light 134 to an IR camera to generate an IR image of the surgical field, and may direct visible light 132 to a visible camera to generate a visible image of the surgical field. Controller 162 may be used to display visible and IR images from visible/NIR imaging system 130 at display 136, similarly to or in conjunction with OCT images from OCT system 160, as described above. Various additional details of different implementations of visible/NIR imaging system 130 are described below with respect to FIGS. 2A-2D, 3 and 4.

Figure 6:
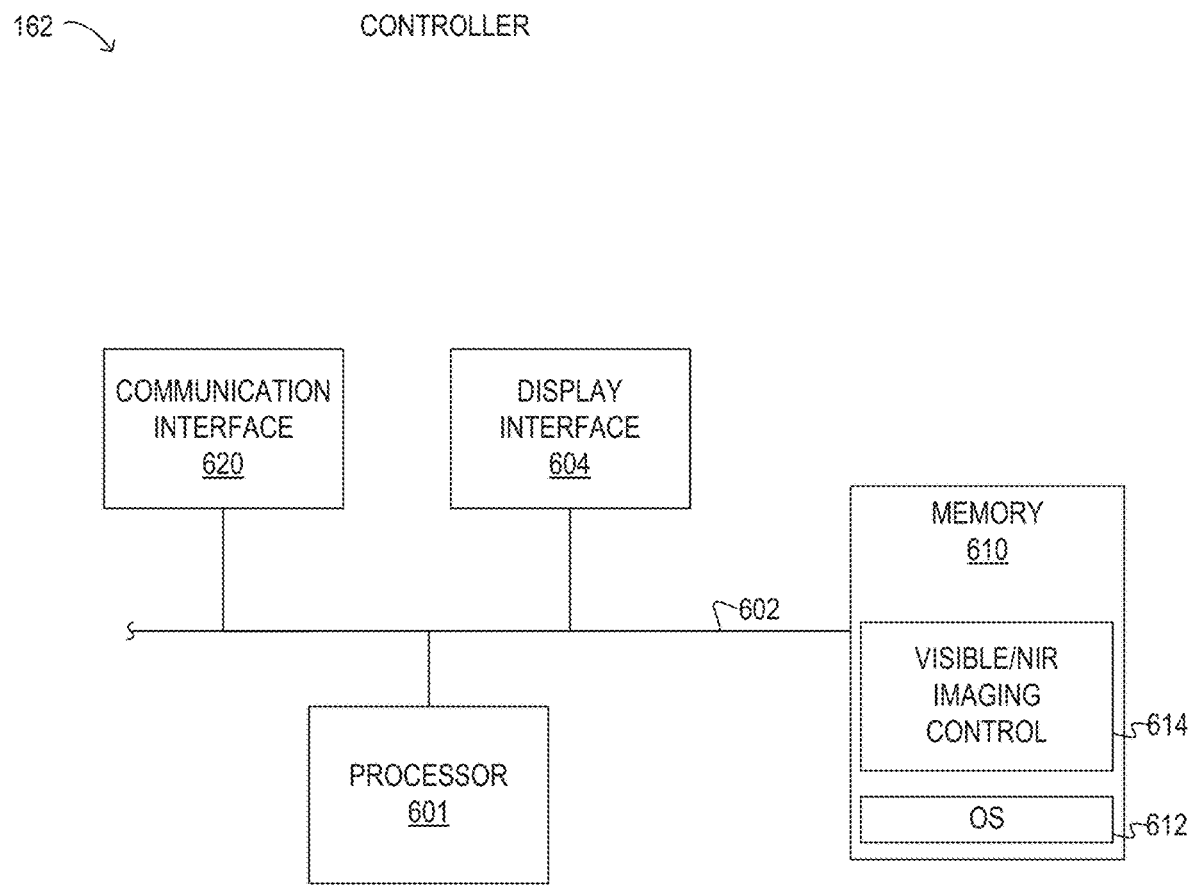
FIG. 6 is a depiction of selected elements of a controller.

In FIG. 1, controller 162 may have an electrical interface with display 136, for example, for outputting display data (see also FIG. 6). Controller 162 may output a display image to display 136 that is viewed at binoculars 126 using from multi-beam splitter 128. Because the electrical interface to controller 162 may support digital image data, controller 162 may perform image processing in real-time with relatively high frame refresh rates, such that a user of surgical microscope 120 may experience substantially instantaneous feedback to user input for controlling displayed images of eye 110, as well as other operations. Display 104 may be implemented as a liquid crystal display screen (LCD), a light emitting diode (LED) display, such as an organic LED (OLED), a computer monitor, a television or the like, a projector, a digital light processing (DLP) engine, or a liquid crystal on silicon (LCoS) device, among other types of display devices. Display 136 may comply with a display standard for the corresponding type of display, such as video graphics array (VGA), extended graphics array (XGA), digital visual interface (DVI), high-definition multimedia interface (HDMI), among other standards. In certain implementations, display 136 may be a miniature device that is integrated with visible/NIR imaging system 130, such as on a common optical device.

As shown in FIG. 1, instrument 100 includes visible/NIR imaging system 130 that is integrated with surgical microscope 120 in a manner that does not increase the stack height of surgical microscope 120, given by a distance between objective lens 124 and binoculars 126. The stack height of surgical microscope 120 may be an important ergonomic factor for the user. For example, the ergonomic desirability of surgical microscope 120 may be significantly reduced when the stack height is too large, thereby making operation of surgical microscope 120 difficult for users below a certain height or having a certain arm length. In instrument 100, the stack height associated with visible/NIR imaging system 130 is not increased, at least in part, due to the functionality of multi-beam splitter 128, as explained above. Furthermore, the optical components included with visible/NIR imaging system 130, along with display 136, as described in detail in the following figures, may be arranged in a plane that is perpendicular to optical paths 154 (as shown in FIG. 1), perpendicular to the stack height, perpendicular to an optical axis of objective lens 124, or perpendicular to an optical axis of eye 110. The arrangement of visible/NIR imaging system 130 in the plane, as described in detail in the following figures, may enable the compact microscopy stack having a relatively small stack height, as shown in FIG. 1, which is desirable.

Modifications, additions, or omissions may be made to surgical microscopy scanning instrument 100 without departing from the scope of the disclosure. The components and elements of surgical microscopy scanning instrument 100, as described herein, may be integrated or separated according to particular applications. Surgical microscopy scanning instrument 100 may be implemented using more, fewer, or different components.

Referring now to FIGS. 2A-2D, 3, and 4, different depictions of particular implementations of visible/NIR imaging system 130 are shown. Visible/NIR imaging systems 130 in FIGS. 2A-2D, 3, and 4 are exemplary implementations that are schematically depicted for descriptive purposes, and are not necessarily drawn to scale or accurate perspective. Visible/NIR imaging systems 130 in FIGS. 2A-2D, 3, and 4 are shown and described in a perspective view to show 3-dimensional optical arrangements of various components. Visible/NIR imaging systems 130 in FIGS. 2A-2D, 3, and 4 may be implemented using more, fewer, or different components. In FIGS. 2A-2D, 3, and 4, visible/NIR imaging systems 130 are shown and described with respect to optical paths, beams, and optical components to enable integration and use with surgical microscope 120 (see FIG. 1). For descriptive clarity, certain elements of surgical microscope 120 and surgical microscopy scanning instrument 100 have been omitted from FIGS. 2A-2D, 3, and 4, but it will be understood that visible/NIR imaging systems 130 may be used with surgical microscopy scanning instrument 100, as described herein. Furthermore, in FIGS. 2A-2D, 3, and 4, display 136, oculars 126, and optical path 154 are included in various depictions for descriptive clarity of the optical integration and it will be understood that such elements may be external to any particular visible/NIR imaging system 130. In FIGS. 2A-2D, 3, and 4, an imaging path 202 shows a planar optical configuration of optical paths included with visible/NIR imaging system 130, while a display path 204 shows a planar optical configuration of optical paths associated with display 136. In various implementations, imaging path 202 and display path 204 may be aligned to the same plane.

In FIG. 2A, a visible/NIR imaging system 130-1 is shown in a left channel configuration in which imaging path 202 and display path 204 are integrated with a single ocular, shown arbitrarily as left ocular 154-L with left optical path 154-L. Specifically, in imaging path 202 of visible/NIR imaging system 130-1, a first portion of visible light 132-1 arriving from objective lens 124 (see FIG. 1) along left optical path 154-L to multi-beam splitter 128 is transmitted to left ocular 154-L along left optical path 154-L. A second portion of visible light 132-1 is reflected by multi-beam splitter 128 to imaging path 202 to a dichroic mirror 210. Dichroic mirror 210 may be used to transmit the second portion of visible light 132-1 (carrying a visible image of the surgical field) to a visible camera 232, which may be a digital camera. The first portion of visible light 132-1 may be about twice the intensity of the second portion of visible light 132-1 in particular implementations. At the same time, in visible/NIR imaging system 130-1, NIR light 134 (carrying an IR image of the surgical field) arriving from objective lens 124 along left optical path 154-L to multi-beam splitter 128 is reflected by dichroic mirror 210 towards an IR camera 234, which may be a digital camera. In various implementations, visible camera 232 may be oriented perpendicular to IR camera 234. It will be understood that the dichroic operation of dichroic mirror 210 may be reversed, such that visible camera 232 and IR camera 234 may be exchanged in position relative to dichroic mirror 210. In display path 204 of visible/NIR imaging system 130-1, display 136 may output display light 132-2 (carrying a visible display image generated by display 136) to an opposing face of multi-beam splitter 128 from imaging path 202. Multi-beam splitter 128 may be particularly constructed to reflect a substantial portion or substantially all of display light 132-2 towards left ocular 126-L along left optical path 154-L.

Figure 2B:
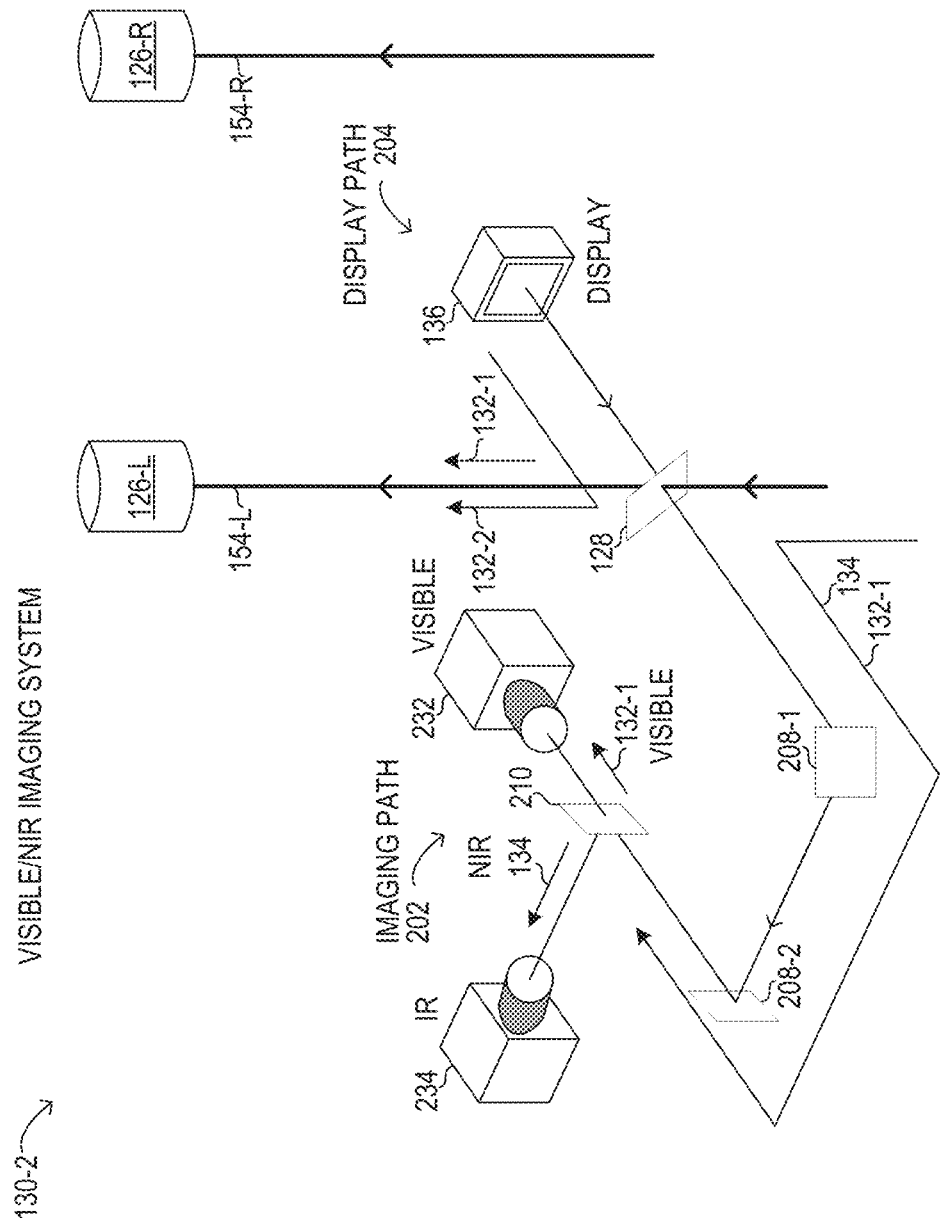

In FIG. 2B, a visible/NIR imaging system 130-2 is shown in another left channel configuration in which imaging path 202 and display path 204 are integrated with a single ocular, shown arbitrarily as left ocular 154-L with left optical path 154-L. Specifically, in imaging path 202 of visible/NIR imaging system 130-2, a first portion of visible light 132-1 arriving from objective lens 124 (see FIG. 1) along left optical path 154-L to multi-beam splitter 128 is transmitted to left ocular 154-L along left optical path 154-L. A second portion of visible light 132-1 is reflected by multi-beam splitter 128 to imaging path 202, where a first mirror 208-1 and a second mirror 208-2 are used to divert the second portion of visible light 132-1 to dichroic mirror 210. Dichroic mirror 210 may be used to transmit the second portion of visible light 132-1 (carrying a visible image of the surgical field) to visible camera 232. The first portion of visible light 132-1 may be about twice the intensity of the second portion of visible light 132-1 in particular implementations. At the same time, in visible/NIR imaging system 130-2, NIR light 134 (carrying an IR image of the surgical field) travels along imaging path 202 (diverted by mirrors 208-1, 208-2) with the second portion of visible light 132-1 to dichroic mirror 210. NIR light 134 is then reflected by dichroic mirror 210 towards an IR camera 234. In various implementations, visible camera 232 may be oriented perpendicular to IR camera 234. It will be understood that the dichroic operation of dichroic mirror 210 may be reversed, such that visible camera 232 and IR camera 234 may be exchanged in position relative to dichroic mirror 210. In display path 204 of visible/NIR imaging system 130-2, display 136 may output display light 132-2 (carrying a visible display image generated by display 136) to an opposing face of multi-beam splitter 128 from imaging path 202. Multi-beam splitter 128 may be particularly constructed to reflect a substantial portion or substantially all of display light 132-2 towards left ocular 126-L along left optical path 154-L.

Figure 2C:
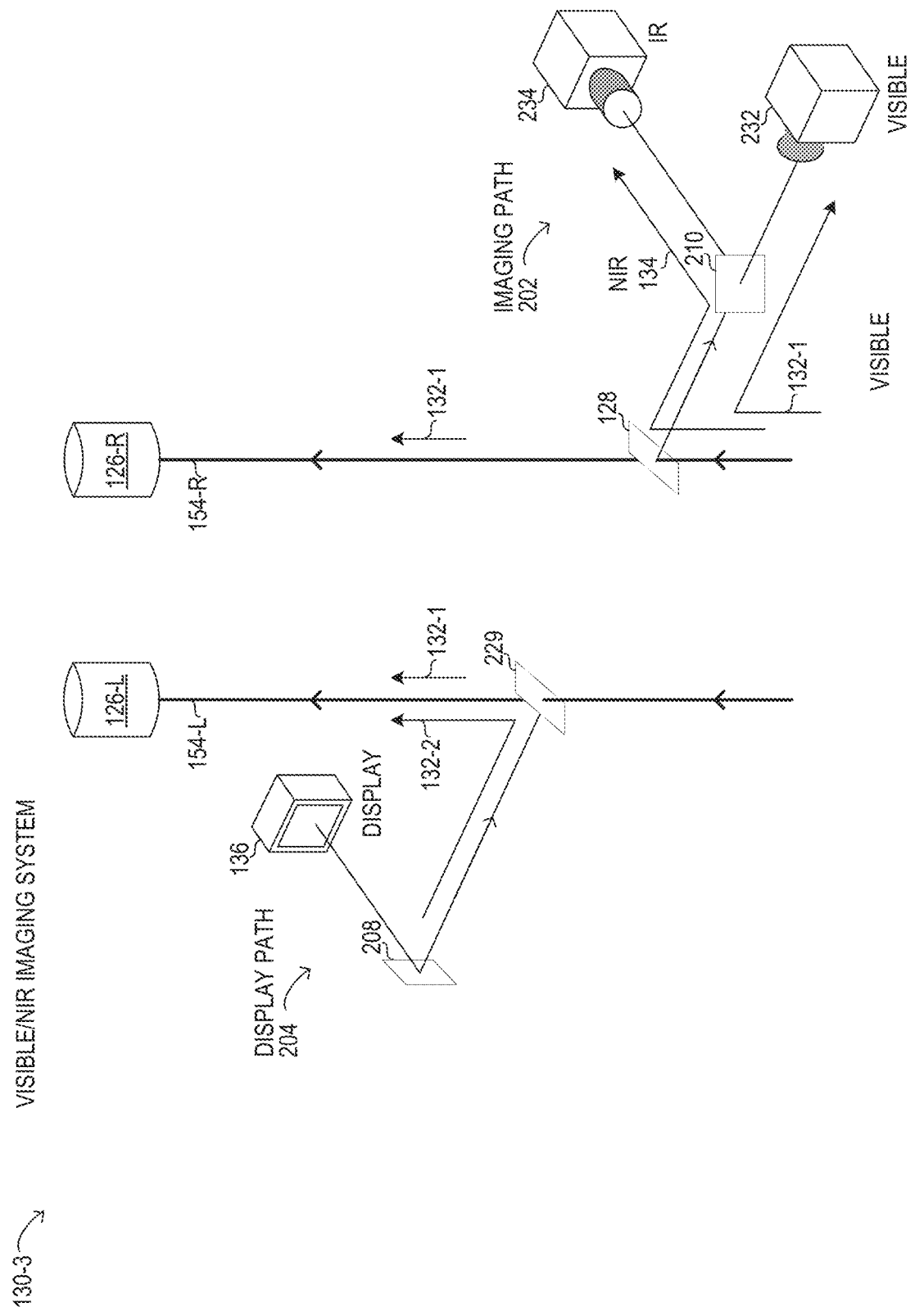

In FIG. 2C, a visible/NIR imaging system 130-3 is shown in a binocular configuration in which imaging path 202 and display path 204 are each integrated with a different ocular, corresponding to the configuration shown in FIG. 1. Specifically, in imaging path 202 of visible/NIR imaging system 130-3, a first portion of visible light 132-1 arriving from objective lens 124 (see FIG. 1) along right optical path 154-R to multi-beam splitter 128 is transmitted to right ocular 154-R along right optical path 154-R. A second portion of visible light 132-1 is reflected by multi-beam splitter 128 to imaging path 202 to dichroic mirror 210. Dichroic mirror 210 may be used to transmit the second portion of visible light 132-1 (carrying a visible image of the surgical field) to visible camera 232. The first portion of visible light 132-1 may be about twice the intensity of the second portion of visible light 132-1 in particular implementations. At the same time, in visible/NIR imaging system 130-3, NIR light 134 (carrying an IR image of the surgical field) travels along imaging path 202 with the second portion of visible light 132-1 to dichroic mirror 210. NIR light 134 is then reflected by dichroic mirror 210 towards an IR camera 234. In various implementations, visible camera 232 may be oriented perpendicular to IR camera 234. It will be understood that the dichroic operation of dichroic mirror 210 may be reversed, such that visible camera 232 and IR camera 234 may be exchanged in position relative to dichroic mirror 210. In display path 204 of visible/NIR imaging system 130-3, display 136 may output display light 132-2 (carrying a visible display image generated by display 136) to partial mirror 229, which reflects a substantial portion or substantially all of display light 132-2 towards left ocular 126-L along left optical path 154-L. At the same time, in FIG. 2C, partial mirror 229 transmits visible light 132-1 towards left ocular 126-L along left optical path 154-L.

Figure 2D:
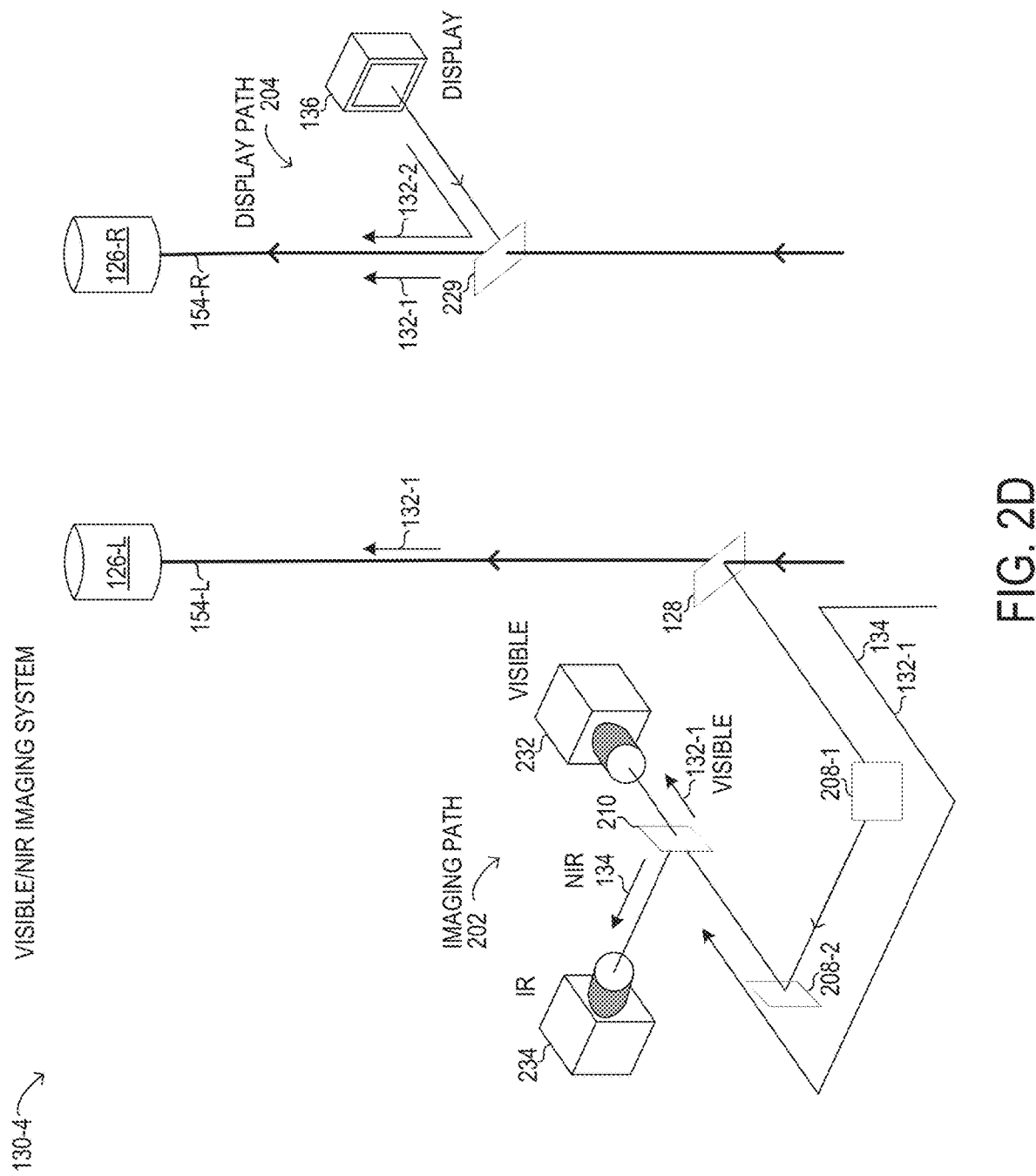

In FIG. 2D, a visible/NIR imaging system 130-4 is shown in another monoscopic configuration in which imaging path 202 and display path 204 are each integrated with a different ocular, corresponding to the configuration shown in FIG. 1. Specifically, in imaging path 202 of visible/NIR imaging system 130-4, a first portion of visible light 132-1 arriving from objective lens 124 (see FIG. 1) along left optical path 154-L to multi-beam splitter 128 is transmitted to left ocular 154-L along left optical path 154-L. A second portion of visible light 132-1 is reflected by multi-beam splitter 128 to imaging path 202, where a first mirror 208-1 and a second mirror 208-2 are used to divert the second portion of visible light 132-1 to dichroic mirror 210. Dichroic mirror 210 may be used to transmit the second portion of visible light 132-1 (carrying a visible image of the surgical field) to visible camera 232. The first portion of visible light 132-1 may be about twice the intensity of the second portion of visible light 132-1 in particular implementations. At the same time, in visible/NIR imaging system 130-4, NIR light 134 (carrying an IR image of the surgical field) travels along imaging path 202 with the second portion of visible light 132-1 to dichroic mirror 210. NIR light 134 is then reflected by dichroic mirror 210 towards an IR camera 234. In various implementations, visible camera 232 may be oriented perpendicular to IR camera 234. It will be understood that the dichroic operation of dichroic mirror 210 may be reversed, such that visible camera 232 and IR camera 234 may be exchanged in position relative to dichroic mirror 210. In display path 204 of visible/NIR imaging system 130-4, display 136 may output display light 132-2 (carrying a visible display image generated by display 136) to partial mirror 229, which reflects a substantial portion or substantially all of display light 132-2 towards right ocular 126-R along right optical path 154-R. At the same time, in FIG. 2D, partial mirror 229 transmits visible light 132-1 towards right ocular 126-R along right optical path 154-R.

Figure 3A:
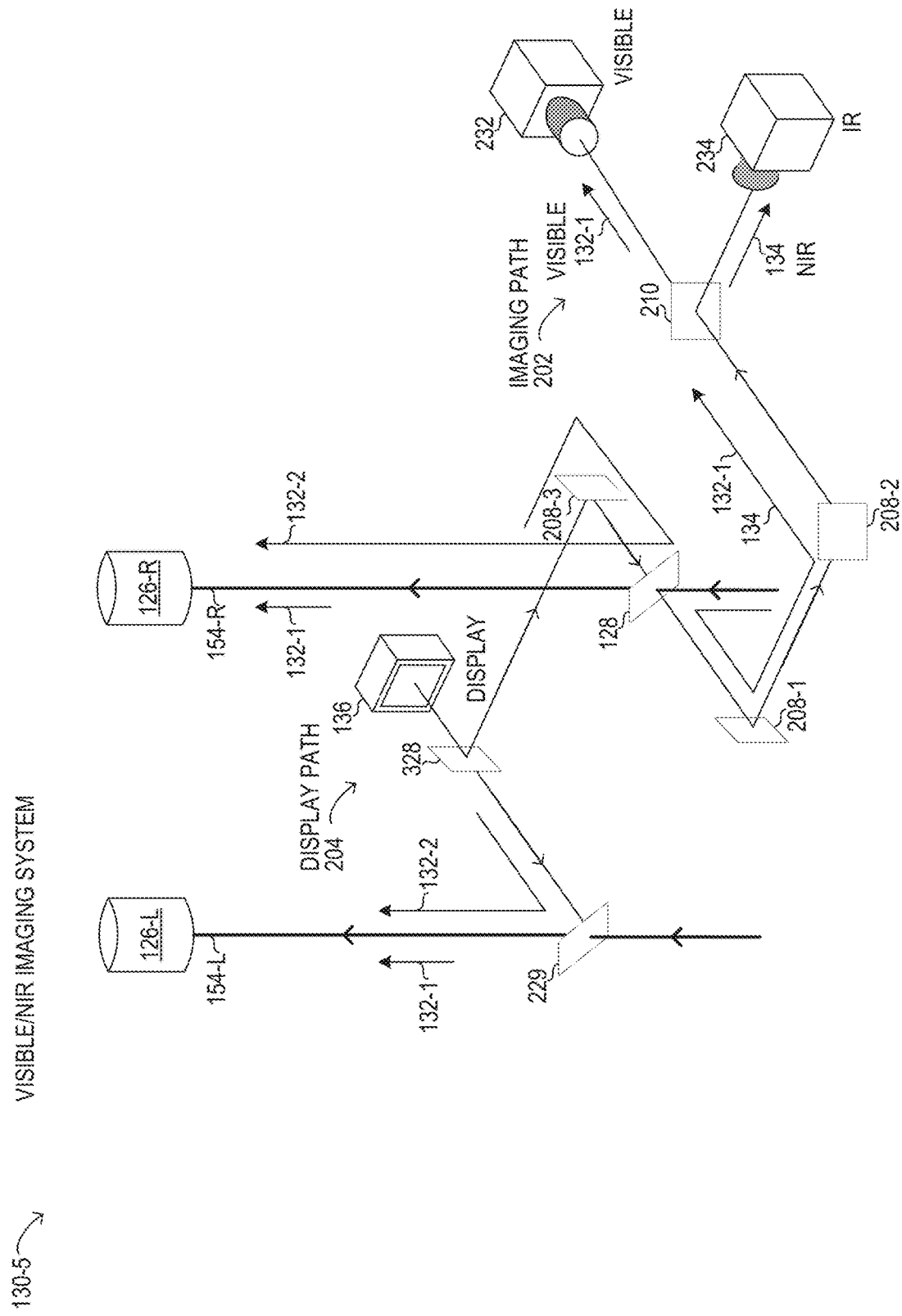
FIGS. 3A and 3B are depictions of selected elements of different visible/NIR imaging systems.

In FIG. 3A, a visible/NIR imaging system 130-5 is shown in a stereoscopic configuration in which display path 204 outputs a display image to both oculars, while imaging path 202 is integrated with one ocular. In FIG. 3A, display 136 may support 3D display. Specifically, in imaging path 202 of visible/NIR imaging system 130-5, a first portion of visible light 132-1 arriving from objective lens 124 (see FIG. 1) along right optical path 154-R to multi-beam splitter 128 is transmitted to right ocular 154-R along right optical path 154-L. A second portion of visible light 132-1 is reflected by multi-beam splitter 128 to imaging path 202, where a first mirror 208-1 and a second mirror 208-2 are used to divert the second portion of visible light 132-1 to dichroic mirror 210. Dichroic mirror 210 may be used to transmit the second portion of visible light 132-1 (carrying a visible image of the surgical field) to visible camera 232. The first portion of visible light 132-1 may be about twice the intensity of the second portion of visible light 132-1 in particular implementations. At the same time, in visible/NIR imaging system 130-5, NIR light 134 (carrying an IR image of the surgical field) travels along imaging path 202 with the second portion of visible light 132-1 to dichroic mirror 210. NIR light 134 is then reflected by dichroic mirror 210 towards an IR camera 234. In various implementations, visible camera 232 may be oriented perpendicular to IR camera 234. It will be understood that the dichroic operation of dichroic mirror 210 may be reversed, such that visible camera 232 and IR camera 234 may be exchanged in position relative to dichroic mirror 210. In display path 204 of visible/NIR imaging system 130-5, display 136 may output display light 132-2 (carrying a visible display image generated by display 136) to a beam splitter 328 that splits display light 132-2 into a left and a right portion. The left portion of display light 132-2 is output to partial mirror 229, which reflects a substantial portion or substantially all of the left portion of display light 132-2 towards left ocular 126-L along left optical path 154-L. In FIG. 3A, the right portion of display light 132-2 is reflected by a mirror 208-3 towards multi-beam splitter 128 for reflection towards right ocular 126-R along right optical path 154-R.

Figure 3B:
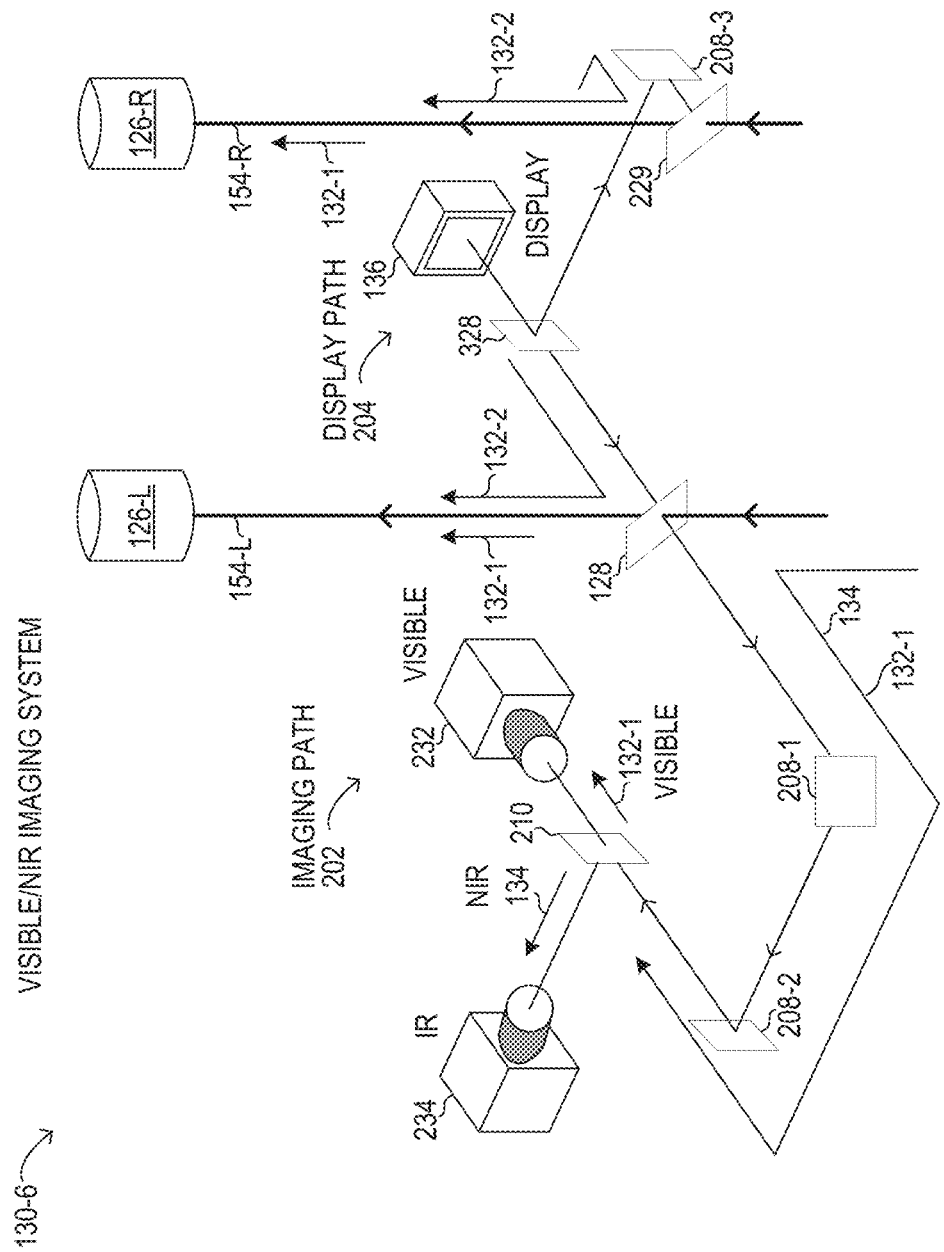

In FIG. 3B, a visible/NIR imaging system 130-6 is shown in a stereoscopic configuration in which display path 204 outputs a display image to both oculars, while imaging path 202 is integrated with one ocular. In FIG. 3B, display 136 may support 3D display. Specifically, in imaging path 202 of visible/NIR imaging system 130-6, a first portion of visible light 132-1 arriving from objective lens 124 (see FIG. 1) along left optical path 154-L to multi-beam splitter 128 is transmitted to left ocular 154-L along left optical path 154-L. A second portion of visible light 132-1 is reflected by multi-beam splitter 128 to imaging path 202, where a first mirror 208-1 and a second mirror 208-2 are used to divert the second portion of visible light 132-1 to dichroic mirror 210. Dichroic mirror 210 may be used to transmit the second portion of visible light 132-1 (carrying a visible image of the surgical field) to visible camera 232. The first portion of visible light 132-1 may be about twice the intensity of the second portion of visible light 132-1 in particular implementations. At the same time, in visible/NIR imaging system 130-6, NIR light 134 (carrying an IR image of the surgical field) travels along imaging path 202 with the second portion of visible light 132-1 to dichroic mirror 210. NIR light 134 is then reflected by dichroic mirror 210 towards an IR camera 234. In various implementations, visible camera 232 may be oriented perpendicular to IR camera 234. It will be understood that the dichroic operation of dichroic mirror 210 may be reversed, such that visible camera 232 and IR camera 234 may be exchanged in position relative to dichroic mirror 210. In display path 204 of visible/NIR imaging system 130-6, display 136 may output display light 132-2 (carrying a visible display image generated by display 136) to a beam splitter 328 that splits display light 132-2 into a left and a right portion. The right portion of display light 132-2 is reflected by a mirror 208-3 towards partial mirror 229, which reflects a substantial portion or substantially all of the right portion of display light 132-2 towards right ocular 126-R along right optical path 154-R. In FIG. 3B, the left portion of display light 132-2 is output to multi-beam splitter 128 for reflection towards left ocular 126-L along left optical path 154-L.

Figure 4:
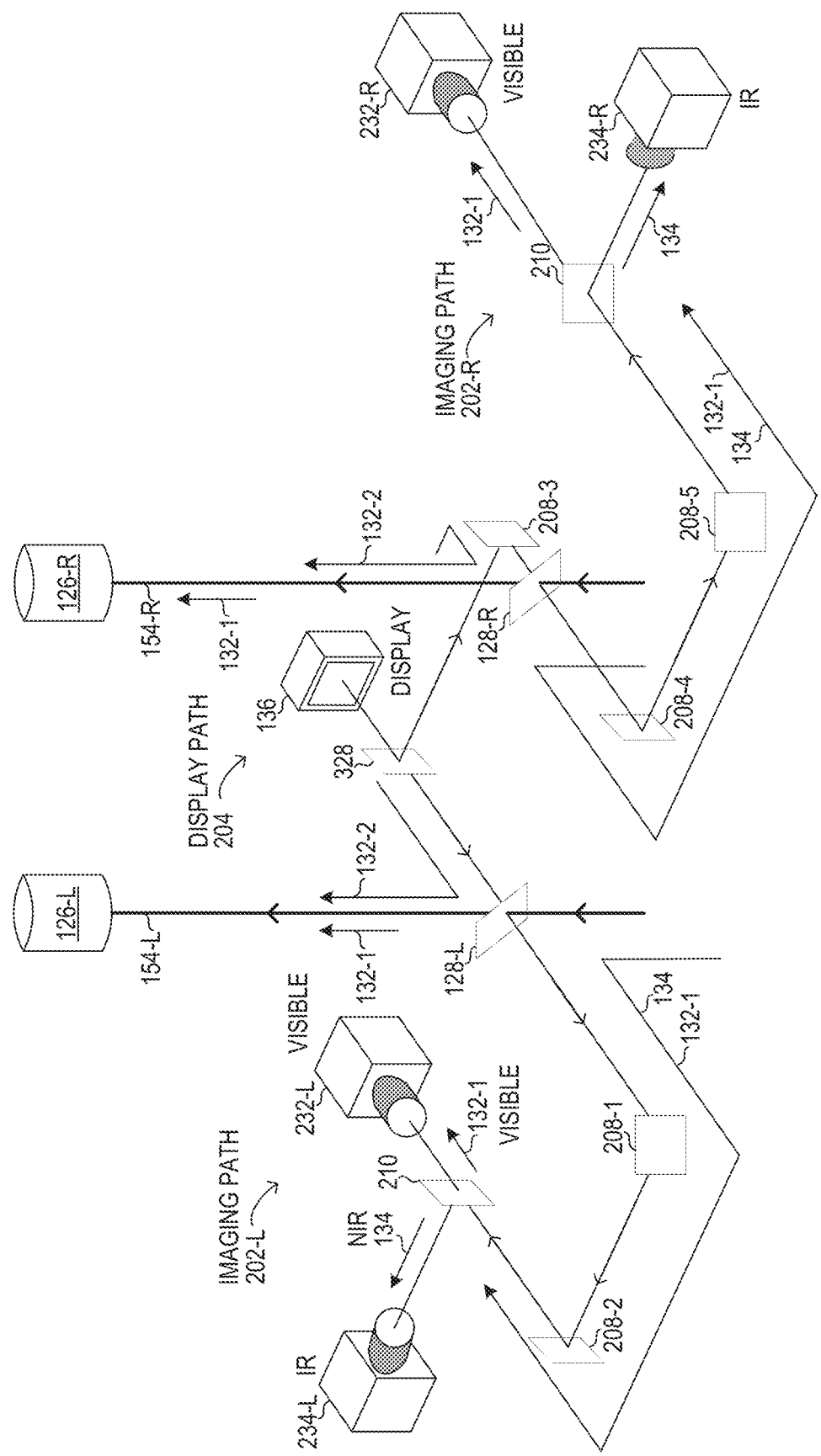
FIG. 4 is a depiction of selected elements of a stereoscopic visible/NIR imaging system.

In FIG. 4, a visible/NIR imaging system 130-7 is shown in a full stereoscopic configuration in which display path 204 outputs a display image to both oculars, while two separate imaging paths 202-L and 202-R are integrated with respective oculars. In FIG. 4, display 136 may support 3D display.

Specifically, in imaging path 202-L of visible/NIR imaging system 130-7, a first portion of visible light 132-1 arriving from objective lens 124 (see FIG. 1) along left optical path 154-L to left multi-beam splitter 128-L is transmitted to left ocular 154-L along left optical path 154-L. A second portion of visible light 132-1 is reflected by left multi-beam splitter 128-L to left imaging path 202-L, where a first mirror 208-1 and a second mirror 208-2 are used to divert the second portion of visible light 132-1 to dichroic mirror 210 in left imaging path 202-L. Dichroic mirror 210 may be used to transmit the second portion of visible light 132-1 (carrying a visible image of the surgical field) to left visible camera 232-L. The first portion of visible light 132-1 may be about twice the intensity of the second portion of visible light 132-1 in particular implementations. At the same time, in visible/NIR imaging system 130-7, NIR light 134 (carrying an IR image of the surgical field) travels along imaging path 202-L with the second portion of visible light 132-1 to dichroic mirror 210 in imaging path 202-L. NIR light 134 is then reflected by dichroic mirror 210 towards a left IR camera 234-L. In various implementations, visible camera 232 may be oriented perpendicular to left IR camera 234. It will be understood that the dichroic operation of dichroic mirror 210 may be reversed, such that left visible camera 232-L and right IR camera 234-L may be exchanged in position relative to dichroic mirror 210 in imaging path 202-L.

In display path 204 of visible/NIR imaging system 130-7, display 136 may output display light 132-2 (carrying a visible display image generated by display 136) to a beam splitter 328 that splits display light 132-2 into a left and a right portion. The right portion of display light 132-2 is reflected by a third mirror 208-3 towards partial mirror 229, which reflects a substantial portion or substantially all of the right portion of display light 132-2 towards right ocular 126-R along right optical path 154-R. In FIG. 4, the left portion of display light 132-2 is output to multi-beam splitter 128 for reflection towards left ocular 126-L along left optical path 154-L.

In FIG. 4, in right imaging path 202-R of visible/NIR imaging system 130-6, a first portion of visible light 132-1 arriving from objective lens 124 (see FIG. 1) along right optical path 154-R to a right multi-beam splitter 128-R is transmitted to right ocular 154-R along right optical path 154-L. A second portion of visible light 132-1 is reflected by right multi-beam splitter 128-R to right imaging path 202-R, where a fourth mirror 208-4 and a fifth mirror 208-5 are used to divert the second portion of visible light 132-1 to dichroic mirror 210 in right imaging path 202-R. Dichroic mirror 210 may be used to transmit the second portion of visible light 132-1 (carrying a visible image of the surgical field) to a right visible camera 232-R. The first portion of visible light 132-1 may be about twice the intensity of the second portion of visible light 132-1 in particular implementations. At the same time, in visible/NIR imaging system 130-7, NIR light 134 (carrying an IR image of the surgical field) travels along right imaging path 202-R with the second portion of visible light 132-1 to dichroic mirror 210. NIR light 134 is then reflected by dichroic mirror 210 towards a right IR camera 234-R. In various implementations, right visible camera 232-R may be oriented perpendicular to right IR camera 234-R. It will be understood that the dichroic operation of dichroic mirror 210 may be reversed in right imaging path 202-R, such that right visible camera 232-R and right IR camera 234-R may be exchanged in position relative to dichroic mirror 210.

Referring now to FIG. 5, a flow chart of selected elements of a method 500 for performing ophthalmic surgery, as described herein, is depicted in flowchart form. Method 500 describes steps and procedures that controller 162 may perform while a user operates surgical microscopy scanning instrument 100 to view the fundus of an eye and perform surgical procedures based on the view of the fundus. For example, method 500 may be executed by visible/NIR imaging control 614 (see FIG. 6). In particular implementations, OCT system 160 may perform at least some operations described below in method 500. It is noted that certain operations described in method 500 may be optional or may be rearranged in different implementations.

Method 500 may begin, at step 502, by scanning a surgical field using an OCT scanning system coupled to a surgical microscope, the surgical microscope used to view visible light from the surgical field, where the OCT scanning system projects NIR light onto the surgical field for the scanning of the surgical field. At step 504, using a multi-beam splitter in an optical path transmitting the visible light to a first ocular of the surgical microscope, a first portion of the NIR light and a second portion of the visible light are diverted to an imaging path of the surgical microscope, where the imaging path is in a plane perpendicular to the optical path. At step 506, using a dichroic mirror in the imaging path, the first portion of the NIR light is split from the second portion of the visible light. At step 508, an IR image of the surgical field is generated from the first portion of the NIR light using an IR camera, the IR image indicating a location in the surgical field of the scanning of the surgical field. At step 510, a visible image of the surgical field is generated from the second portion of the visible light using a visible camera, where the visible camera and the IR camera are positioned in the plane. At step 512, the acquired IR image is sent to a controller used to generate display light for viewing at a second ocular of the surgical microscope, where at least a portion of the display light follows a path of visible light transmitted to the second ocular. At step 514, the acquired visible image is sent to the controller, where at least a portion of the display light follows the path of the visible light transmitted to the second ocular. The display light in steps 512 and 514 may include or represent overlay information for overlaying on the view of the surgical field.

Referring now to FIG. 6, a depiction of selected elements of controller 162, described above with respect to FIG. 1, is presented. In the implementation depicted in FIG. 6, controller 162 includes processor 601 coupled via shared bus 602 to memory media collectively identified as memory 610.

Controller 162, as depicted in FIG. 6, further includes communication interface 620 that can interface controller 162 to various external entities, such as OCT system 160, visible/NIR imaging system 130, and display 136, among other devices. In some implementations, communication interface 620 is operable to enable controller 162 to connect to a network (not shown in FIG. 6). In some implementations suitable for combined near infrared imaging and visible imaging in a compact microscope stack, controller 162, as depicted in FIG. 6, includes display interface 604 that connects shared bus 602, or another bus, with an output port for one or more displays, such as display 136 or an external display.

In FIG. 6, memory 610 encompasses persistent and volatile media, fixed and removable media, and magnetic and semiconductor media. Memory 610 is operable to store instructions, data, or both. Memory 610 as shown includes sets or sequences of instructions, namely, an operating system 312, and a visible/NIR imaging control application 614. Operating system 612 may be a UNIX or UNIX-like operating system, a Windows® family operating system, or another suitable operating system.

Figure 7:
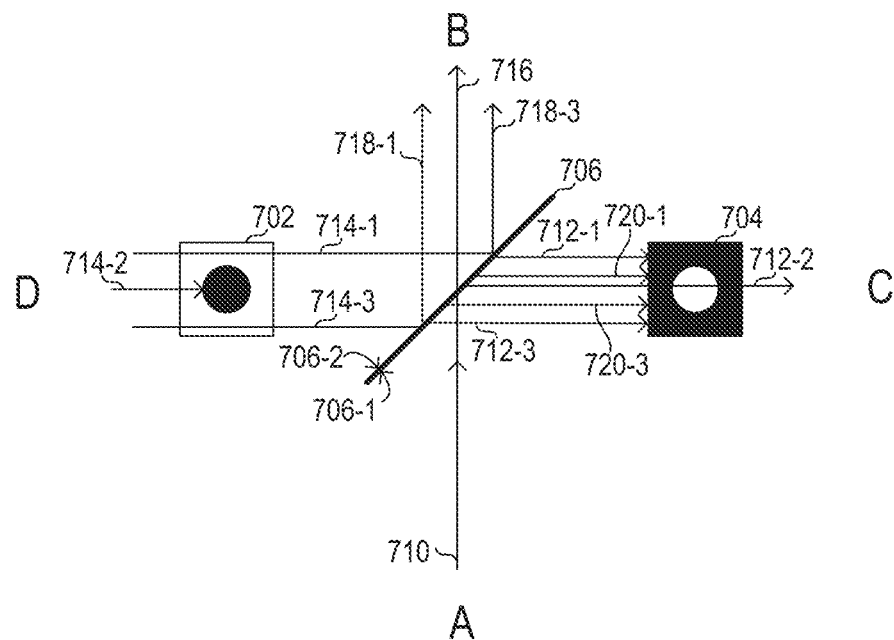
FIG. 7 is a depiction of a multi-beam splitter.

Referring now to FIG. 7, a depiction of a multi-beam splitter 128-1 for multi-beam splitting using spatial beam separation is shown. Multi-beam splitter 128-1 is not drawn to scale or perspective but is a schematic representation. In FIG. 7, internal details describing the operation of multi-beam splitter 128, as described above, are explained. Various implementations and configurations of multi-beam splitter 128 are described in U.S. Patent Application titled "MULTI-BEAM SPLITTING USING SPATIAL BEAM SEPARATION" filed concurrently with the present application. Multi-beam splitter 128-1 is shown in a generic configuration with a first source A, a second source D, a first output B, and a second output C. For example, in comparison to instrument 100 in FIG. 1, first source A may be an object being viewed using surgical microscope 120, such as eye 110, while first output B may be a viewing port of the microscope, such as ocular 126. Furthermore, second source D may be a source of overlay content, such as display 136, while second output C may be a sensor port for acquisition of images of the object at first source A, such as OCT system 160 or visible/NIR imaging system 130 in various implementations.

In FIG. 7, a first beam 710 arrives from first source A at a partial mirror 706 at a first surface 706-1. Because partial mirror 706 is configured to partially reflect and partially transmit incoming light at first surface 706-1, partial mirror 706 transmits a first partial beam 716 from first beam 710, and reflects a second partial beam 712 from first beam 710. Specifically, second partial beam 712 reflected from first surface 706-1 is shown comprising beams 712-1, 712-2, 712-3 over an area corresponding to an aperture filter 704 placed at second output C. Aperture filter 704 comprises an opaque field with a circular aperture having a second radius (r2) that is transparent and serves as an aperture for second partial beam 712-2 that arrives at second output C, while second partial beams 712-1, 712-2 are blocked at aperture filter 704 because they arrive at peripheral portions of aperture filter 704 outside of the aperture. Meanwhile first partial beam 716 is transmitted to first output B.

Also in FIG. 7, a second beam 714, shown as beams 714-1, 714-2, 714-3, arrives from first source D at a spot filter 702. Spot filter 702 comprises a transparent field with a circular opaque spot having a first radius (r1) that may be comparable to second radius (r2) of aperture filter 704. In particular, first radius (r1) may be greater than or equal to second radius (r2). Accordingly, peripheral portions 714-1, 714-3 of second beam 714 arrive at a second surface 706-2 of partial mirror 706, while a central portion 714-2 is blocked at spot filter 702. Because partial mirror 706 is configured to partially reflect and partially transmit incoming light at second surface 706-2, partial mirror 706 reflects a third partial beam 718, shown as peripheral portions 718-1, 718-3 towards first output B, such that third partial beam 718 is coaxially superimposed with first partial beam 716, which enables the overlay content (or overlay information) from second source D to be overlaid with the content from first source A at first output B. Concurrently, second surface 706-2 also transmits a fourth partial beam 720 from second beam 714 (peripheral portions 714-1, 714-3) such that only peripheral portions of fourth partial beam 720-1, 720-3, corresponding to the transparent field of spot filter 702, are transmitted to second output C. When first radius (r1) is at least as large as, or equal to, second radius (r2), fourth partial beam 720 is accordingly blocked at aperture filter 704, because the opaque field of aperture filter 704 will spatially correspond to the transparent field of spot filter 702. Thus, peripheral portions of fourth partial beam 720-1, 720-3 are blocked by aperture filter 704, and fourth partial beam 720 is blocked by multi-beam splitter 128-1. At the aperture of aperture filter 704, only second partial beam 712-2 arrives, because a central portion of second partial beam 712-2 was blocked at spot filter 702, thereby preventing a central portion of fourth partial beam 720 from interfering with second partial beam 712-2.

It is noted that the absolute values of radii r1 and r2 may be chosen, relative to the size of filters 702, 704 to define a ratio of light coupled to second output C versus to first output B. Because the radii r1 and r2 can be freely chosen, this splitting ratio can be continuously varied as desired. It is further noted that in some implementations, spot filter 702 and aperture filter 704 may be exchanged in position. Spot filter 702 and aperture filter 704 may be implemented using mechanical components or opaque coatings, and the spot or aperture may be variously formed in different shapes, as an alternative to the circular shape shown in FIG. 7 and described above.

In FIG. 7, the reflected and transmitted beam paths may have different geometries in different implementations of multi-beam splitter 128. As shown, first beam 710 along a first optical axis from first source A to first output B may be perpendicular to second beam 714 along a second optical axis from second source D to second output C, while partial mirror 706 may be oriented at 45 degrees relative to both first beam 710 along the first optical axis and second beam 714 along the second optical axis.

Figure 8:
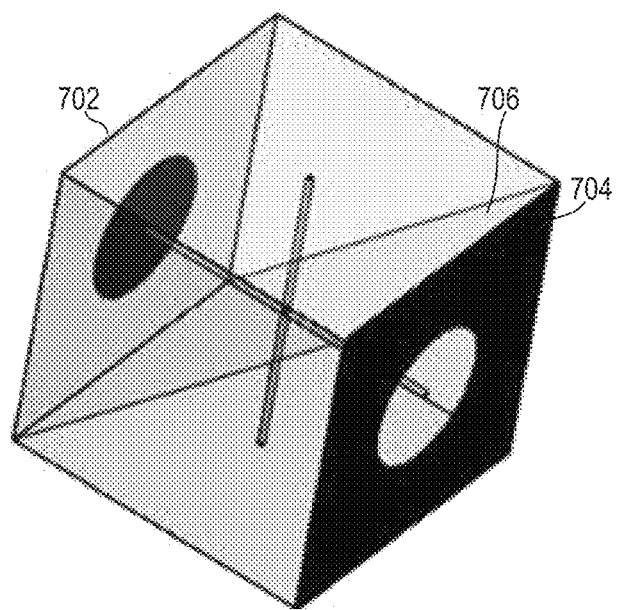
FIG. 8 is a depiction of a multi-beam splitter.

Referring now to FIG. 8, a depiction of a multi-beam splitter 128-2 for multi-beam splitting using spatial beam separation, as described herein, is shown. Multi-beam splitter 128-2 is not drawn to scale or perspective but is a schematic representation shown at a skewed angle for improved visibility. In FIG. 8, an example implementation of multi-beam splitter 128-2 as a cubic optical element is shown. At one face of multi-beam splitter 128-2, spot filter 702 is formed, while aperture filter 704 is formed on an opposing face. Also visible in FIG. 8 is partial mirror 706, which may be formed using an interface between two triangular-shaped prisms. In certain implementations, partial mirror 706 may have dichroic properties.

As disclosed herein, both visible and IR cameras may be integrated without an increase in an optical stack height of a surgical microscope used for ophthalmic surgery. The IR camera may be used to directly and intraoperatively capture a scanning OCT measurement beam, which uses NIR light that is invisible to the human eye. An IR image from the IR camera taken from the same surgical field as displayed intraoperatively to a user of the surgical microscope may be displayed in an ocular to the user, enabling visualization of a location of an OCT scan along with actual visible images of the surgical field.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for performing ophthalmic surgery, the method comprising:
   scanning a surgical field using an optical coherence tomography (OCT) scanning system coupled to a surgical microscope, the surgical microscope used to view visible light from the surgical field, wherein the OCT scanning system projects near-infrared (NIR) light onto the surgical field for the scanning of the surgical field;
   diverting, using a multi-beam splitter in an optical path transmitting the visible light to a first ocular of the surgical microscope, a first portion of the NIR light and a second portion of the visible light to an imaging path of the surgical microscope;
   splitting, using a dichroic mirror in the imaging path, the first portion of the NIR light from the second portion of the visible light;
   generating an infrared (IR) image of the surgical field from the first portion of the NIR light using an IR camera, the IR image indicating a location in the surgical field of the scanning of the surgical field; and
   generating a visible image of the surgical field from the second portion of the visible light using a visible camera, wherein the visible camera and the IR camera are positioned in the plane.

2. The method of claim 1, further comprising:
   acquiring the IR image from the IR camera; and
   sending the IR image to a controller to generate display light for viewing at a second ocular of the surgical microscope, wherein at least a portion of the display light follows a path of visible light transmitted to the second ocular.

3. The method of claim 2, further comprising:
   acquiring the visible image from the visible camera; and
   sending the visible image to the controller, to generate the display light, wherein at least a portion of the display light follows the path of the visible light transmitted to the second ocular.

4. The method of claim 3, wherein the first ocular and the second ocular are the same ocular and the display light is reflected by the multi-beam splitter onto the optical path.

5. The method of claim 3, wherein the first ocular and the second ocular are different oculars and the display light is reflected by a beam combiner onto the visible light transmitted to the second ocular.

6. The method of claim 5, further comprising:
   splitting the display light into a first display beam and a second display beam using a first beam splitter;
   directing the first display beam to the first ocular using the multi-beam splitter; and
   directing the second display beam to the second ocular using the beam combiner.

7. The method of claim 1, wherein the first portion is at least 90% of the NIR light, and wherein the second portion is less than or equal to 30% of the visible light.

8. The method of claim 1, wherein the visible camera and IR camera are oriented perpendicular to each other.

9. The method of claim 1, further comprising:
   diverting, using a second multi-beam splitter in a second optical path transmitting visible light to a second ocular of the surgical microscope different from the first ocular, a third portion of the NIR light and a fourth portion of the visible light to a second imaging path of the surgical microscope, wherein the imaging path and the second imaging path are in the plane;
   splitting, using a second dichroic mirror in the second imaging path, the third portion of the NIR light from the fourth portion of the visible light;
   generating a second IR image of the surgical field from the third portion of the NIR light using a second IR camera, the second IR image indicating the location in the surgical field of the scanning of the surgical field; and
   generating a second visible image of the surgical field from the fourth portion of the visible light using a second visible camera, wherein the second visible camera and the second IR camera are positioned in the plane.

10. The method of claim 9, further comprising:
    acquiring the second IR image from the second IR camera;
    sending the second IR image to the controller to generate second display light for viewing at the second ocular, wherein at least a portion of the second display light including the second IR image follows a path of the visible light transmitted to the second ocular;
    acquiring the second visible image from the second visible camera; and
    sending the second visible image to the controller to generate the second display light, wherein at least a portion of display light including the second visible image follows the path of the visible light transmitted to the second ocular.

11. A surgical microscope for performing ophthalmic surgery, the surgical microscope comprising:
    an optical coherence tomography (OCT) scanning system coupled to the surgical microscope and used for scanning a surgical field, the surgical microscope used to view visible light from the surgical field, wherein the OCT scanning system projects near-infrared (NIR) light onto the surgical field for the scanning of the surgical field;
    a multi-beam splitter in an optical path transmitting the visible light to a first ocular of the surgical microscope, the multi-beam splitter used to divert a first portion of the NIR light and a second portion of the visible light to an imaging path of the surgical microscope;
    a dichroic mirror in the imaging path used for splitting the first portion of the NIR light from the second portion of the visible light;
    an infrared (IR) camera used to generate an IR image of the surgical field from the first portion of the NIR light, the IR image indicating a location in the surgical field of the scanning of the surgical field; and
    a visible camera used to generate a visible image of the surgical field from the second portion of the visible light, wherein the visible camera and the IR camera are positioned in the plane.

12. The surgical microscope of claim 11, further comprising:
    a controller used to acquire the IR image from the IR camera and generate overlay information; and a display receiving overlay information from the controller, the display used to output display light for viewing at a second ocular of the surgical microscope, wherein at least a portion of the display light follows a path of visible light transmitted to the second ocular.

13. The surgical microscope of claim 12, further comprising:
the controller used to acquire the visible image from the visible camera; and
the display receiving the visible image from the controller, wherein at least a portion of the display light including the visible image follows the path of visible light transmitted to the second ocular.

14. The surgical microscope of claim 13, wherein the first ocular and the second ocular are the same ocular and the display light is reflected by the multi-beam splitter onto the optical path.

15. The surgical microscope of claim 13, wherein the first ocular and the second ocular are different oculars, and further comprising:
a beam combiner used to reflect the display light onto the visible light transmitted to the second ocular.

16. The surgical microscope of claim 13, further comprising:
a first beam splitter used to split the display light into a first display beam and a second display beam;
the multi-beam splitter used to direct the first display beam to the first ocular; and
the beam combiner used to direct the second display beam to the second ocular.

17. The surgical microscope of claim 11, wherein the first portion is at least 90% of the NIR light, and wherein the second portion is less than or equal to 30% of the visible light.

18. The surgical microscope of claim 11, wherein the visible camera and IR camera are oriented perpendicular to each other.

19. The surgical microscope of claim 11, further comprising:

a second multi-beam splitter in a second optical path transmitting visible light to a second ocular of the surgical microscope different from the first ocular, the second multi-beam splitter used to divert a third portion of the NIR light and a fourth portion of the visible light to a second imaging path of the surgical microscope, wherein the imaging path and the second imaging path are in the plane;
a second dichroic mirror in the second imaging path, the second dichroic mirror used to divert the third portion of the NIR light from the fourth portion of the visible light;
a second IR camera used to generate a second IR image of the surgical field from the third portion of the NIR light, the second IR image indicating the location in the surgical field of the scanning of the surgical field; and
a second visible camera used to generate a second visible image of the surgical field from the fourth portion of the visible light, wherein the second visible camera and the second IR camera are positioned in the plane.

20. The surgical microscope of claim 19, further comprising:
the controller used to acquire the second IR image from the second IR camera and generate the overlay information;
a second display receiving the overlay information from the controller, the second display used to output second display light for viewing at the second ocular, wherein at least a portion of the second display light follows a path of the visible light transmitted to the second ocular;
the controller used to acquire the second visible image from the second visible camera and generate the overlay information; and
the second display receiving the overlay information from the controller, wherein at least a portion of the second display light follows the path of the visible light transmitted to the second ocular.

* * * * *